(12) United States Patent
Saba (10) Patent No.: US 12,186,119 B2
(45) Date of Patent: Jan. 7, 2025

(54) INTERACTIVE MODEL INTERFACE FOR IMAGE SELECTION IN MEDICAL IMAGING SYSTEMS

(71) Applicant: Hologic, Inc., Marlborough, MA (US)

(72) Inventor: Nickolas Saba, San Jose, CA (US)

(73) Assignee: Hologic, Inc., Marlborough, MA (US)

( * ) Notice: Subject to any disclaimer, the term of this patent is extended or adjusted under 35 U.S.C. 154(b) by 212 days.

(21) Appl. No.: 17/903,684

(22) Filed: Sep. 6, 2022

(65) Prior Publication Data

US 2023/0107616 A1    Apr. 6, 2023

Related U.S. Application Data

(60) Provisional application No. 63/252,320, filed on Oct. 5, 2021.

(51) Int. Cl.
| | |
|---|---|
| *A61B 6/46* | (2024.01) |
| *A61B 6/00* | (2006.01) |
| *A61B 6/04* | (2006.01) |
| *A61B 6/50* | (2024.01) |

(52) U.S. Cl.
CPC ............ *A61B 6/502* (2013.01); *A61B 6/0414* (2013.01); *A61B 6/465* (2013.01); *A61B 6/466* (2013.01); *A61B 6/469* (2013.01); *A61B 6/545* (2013.01)

(58) Field of Classification Search
None
See application file for complete search history.

(56) References Cited

U.S. PATENT DOCUMENTS

| | | |
|---|---|---|
| 3,502,878 A | 3/1970 | Stewart |
| 3,863,073 A | 1/1975 | Wagner |
| 3,971,950 A | 7/1976 | Evans et al. |
| 4,160,906 A | 7/1979 | Daniels et al. |
| 4,310,766 A | 1/1982 | Finkenzeller et al. |
| 4,496,557 A | 1/1985 | Malen et al. |

(Continued)

FOREIGN PATENT DOCUMENTS

| | | |
|---|---|---|
| CN | 108135580 | 6/2018 |
| EP | 775467 | 5/1997 |

(Continued)

OTHER PUBLICATIONS

"Later Basics—Adobe Press", published Apr. 6, 2017; https://www.adobepress.com/articles/article.asp?p=2756476&seqNum=4.

(Continued)

*Primary Examiner* — Thomas R Artman
(74) *Attorney, Agent, or Firm* — Merchant & Gould P.C.

(57) ABSTRACT

Systems and methods for determining an image type are disclosed. A user interface includes a visual representation of a breast and a visual representation of a medical imaging system. The visual representation of the medical imaging system includes a visual representation of a detector and either a source or a compression paddle. The visual representation of the medical imaging system may be rotatable and positionable relative to the visual representation of the breast. Based on the relative position and orientation of the visual representation of the medical imaging system relative to the visual representation of the breast, an image type is determined. The image type may be displayed at the user interface.

20 Claims, 7 Drawing Sheets

(56) References Cited

U.S. PATENT DOCUMENTS

| | | |
|---|---|---|
| 4,559,641 A | 12/1985 | Caugant et al. |
| 4,706,269 A | 11/1987 | Reina et al. |
| 4,744,099 A | 5/1988 | Huettenrauch et al. |
| 4,773,086 A | 9/1988 | Fujita et al. |
| 4,773,087 A | 9/1988 | Plewes |
| 4,819,258 A | 4/1989 | Kleinman et al. |
| 4,821,727 A | 4/1989 | Levene et al. |
| 4,969,174 A | 11/1990 | Scheid et al. |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,163,075 A | 11/1992 | Lubinsky et al. |
| 5,164,976 A | 11/1992 | Scheid et al. |
| 5,199,056 A | 3/1993 | Darrah |
| 5,240,011 A | 8/1993 | Assa |
| 5,289,520 A | 2/1994 | Pellegrino et al. |
| 5,359,637 A | 10/1994 | Webber |
| 5,365,562 A | 11/1994 | Toker |
| 5,404,152 A | 4/1995 | Nagai |
| 5,415,169 A | 5/1995 | Siczek et al. |
| 5,426,685 A | 6/1995 | Pellegrino et al. |
| 5,452,367 A | 9/1995 | Bick et al. |
| 5,506,877 A | 4/1996 | Niklason et al. |
| 5,526,394 A | 6/1996 | Siczek et al. |
| 5,539,797 A | 7/1996 | Heidsieck et al. |
| 5,553,111 A | 9/1996 | Moore et al. |
| 5,592,562 A | 1/1997 | Rooks |
| 5,594,769 A | 1/1997 | Pellegrino et al. |
| 5,596,200 A | 1/1997 | Sharma et al. |
| 5,598,454 A | 1/1997 | Franetzki et al. |
| 5,609,152 A | 3/1997 | Pellegrino et al. |
| 5,627,869 A | 5/1997 | Andrew et al. |
| 5,657,362 A | 8/1997 | Giger et al. |
| 5,668,889 A | 9/1997 | Hara |
| 5,719,952 A | 2/1998 | Rooks |
| 5,735,264 A | 4/1998 | Siczek et al. |
| 5,769,086 A | 6/1998 | Ritchart et al. |
| 5,803,912 A | 9/1998 | Siczek et al. |
| 5,818,898 A | 10/1998 | Tsukamoto et al. |
| 5,828,722 A | 10/1998 | Ploetz et al. |
| 5,872,828 A | 2/1999 | Niklason et al. |
| 5,878,104 A | 3/1999 | Ploetz |
| 5,896,437 A | 4/1999 | Ploetz |
| 5,986,662 A | 11/1999 | Argiro et al. |
| 6,005,907 A | 12/1999 | Ploetz |
| 6,022,325 A | 2/2000 | Siczek et al. |
| 6,075,879 A | 6/2000 | Roehrig et al. |
| 6,091,841 A | 7/2000 | Rogers et al. |
| 6,137,527 A | 10/2000 | Abdel-Malek et al. |
| 6,141,398 A | 10/2000 | He et al. |
| 6,149,301 A | 11/2000 | Kautzer et al. |
| 6,175,117 B1 | 1/2001 | Komardin et al. |
| 6,196,715 B1 | 3/2001 | Nambu et al. |
| 6,216,540 B1 | 4/2001 | Nelson et al. |
| 6,219,059 B1 | 4/2001 | Argiro |
| 6,233,473 B1 | 5/2001 | Shepherd et al. |
| 6,243,441 B1 | 6/2001 | Zur |
| 6,256,370 B1 | 7/2001 | Yavuz |
| 6,272,207 B1 | 8/2001 | Tang |
| 6,289,235 B1 | 9/2001 | Webber et al. |
| 6,292,530 B1 | 9/2001 | Yavus et al. |
| 6,327,336 B1 | 12/2001 | Gingold et al. |
| 6,341,156 B1 | 1/2002 | Baetz et al. |
| 6,375,352 B1 | 4/2002 | Hewes et al. |
| 6,411,836 B1 | 6/2002 | Patel et al. |
| 6,415,015 B2 | 7/2002 | Nicolas et al. |
| 6,442,288 B1 | 8/2002 | Haerer et al. |
| 6,459,925 B1 | 10/2002 | Nields et al. |
| 6,501,819 B2 | 12/2002 | Unger et al. |
| 6,515,685 B1 | 2/2003 | Halverson |
| 6,525,713 B1 | 2/2003 | Soeta et al. |
| 6,556,655 B1 | 4/2003 | Chichereau et al. |
| 6,597,762 B1 | 7/2003 | Ferrant et al. |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes et al. |
| 6,638,235 B2 | 10/2003 | Miller et al. |
| 6,647,092 B2 | 11/2003 | Eberhard et al. |
| 6,744,848 B2 | 6/2004 | Stanton et al. |
| 6,748,044 B2 | 6/2004 | Sabol et al. |
| 6,751,285 B2 | 6/2004 | Eberhard et al. |
| 6,751,780 B1 | 6/2004 | Neff et al. |
| 6,758,824 B1 | 7/2004 | Miller et al. |
| 6,813,334 B2 | 11/2004 | Koppe et al. |
| 6,882,700 B2 | 4/2005 | Wang et al. |
| 6,885,724 B2 | 4/2005 | Li et al. |
| 6,912,319 B1 | 6/2005 | Barnes et al. |
| 6,940,943 B2 | 9/2005 | Claus et al. |
| 6,978,040 B2 | 12/2005 | Berestov |
| 6,999,554 B2 | 2/2006 | Mertelmeier |
| 7,025,725 B2 | 4/2006 | Dione et al. |
| 7,110,490 B2 | 9/2006 | Eberhard |
| 7,110,502 B2 | 9/2006 | Tsuji |
| 7,123,684 B2 | 10/2006 | Jing et al. |
| 7,127,091 B2 | 10/2006 | Op De Beek et al. |
| 7,142,633 B2 | 11/2006 | Eberhard et al. |
| 7,245,694 B2 | 7/2007 | Jing et al. |
| 7,315,607 B2 | 1/2008 | Ramsauer |
| 7,319,735 B2 | 1/2008 | Defreitas et al. |
| 7,323,692 B2 | 1/2008 | Rowlands et al. |
| 7,430,272 B2 | 9/2008 | Jing et al. |
| 7,443,949 B2 | 10/2008 | Defreitas et al. |
| 7,577,282 B2 | 8/2009 | Gkanatsios et al. |
| 7,606,801 B2 | 10/2009 | Faitelson et al. |
| 7,630,533 B2 | 12/2009 | Ruth et al. |
| 7,702,142 B2 | 4/2010 | Ren et al. |
| 7,760,924 B2 | 7/2010 | Ruth et al. |
| 7,840,905 B1 | 11/2010 | Weber |
| 8,239,784 B2 | 8/2012 | Hotelling |
| 8,571,289 B2 | 10/2013 | Ruth et al. |
| 8,712,127 B2 | 4/2014 | Ren et al. |
| 8,799,013 B2 * | 8/2014 | Gustafson ............ G16H 30/40 |
| | | 382/128 |
| 8,842,806 B2 * | 9/2014 | Packard ............ A61B 6/0414 |
| | | 378/195 |
| 9,084,579 B2 | 7/2015 | Ren |
| 9,795,357 B2 * | 10/2017 | Carelsen ............... A61B 6/461 |
| 9,811,758 B2 | 11/2017 | Ren |
| 9,962,138 B2 * | 5/2018 | Schweizer ............ A61B 6/467 |
| 10,076,295 B2 * | 9/2018 | Gemmel ............... A61B 6/547 |
| 10,111,631 B2 | 10/2018 | Gkanatsios et al. |
| 10,206,644 B2 * | 2/2019 | Kim .................... A61B 6/0492 |
| 10,248,882 B2 | 4/2019 | Ren |
| 10,679,095 B2 | 6/2020 | Ren |
| 10,922,897 B2 * | 2/2021 | Maeda ................ A61B 6/466 |
| 11,650,672 B2 | 5/2023 | Mellett |
| 11,857,358 B2 | 1/2024 | Liu |
| 12,011,305 B2 * | 6/2024 | Cowles ................ A61B 6/464 |
| 2001/0038681 A1 | 11/2001 | Stanton et al. |
| 2001/0038861 A1 | 11/2001 | Hsu et al. |
| 2002/0012450 A1 | 1/2002 | Tsujii |
| 2002/0050986 A1 | 5/2002 | Inoue et al. |
| 2002/0075997 A1 | 6/2002 | Unger et al. |
| 2003/0018272 A1 | 1/2003 | Treado et al. |
| 2003/0073895 A1 | 4/2003 | Nields et al. |
| 2003/0095624 A1 | 5/2003 | Eberhard et al. |
| 2003/0149364 A1 | 8/2003 | Kapur |
| 2003/0194050 A1 | 10/2003 | Eberhard et al. |
| 2003/0194051 A1 | 10/2003 | Wang et al. |
| 2003/0194115 A1 | 10/2003 | Kaufhold et al. |
| 2003/0194121 A1 | 10/2003 | Eberhard et al. |
| 2003/0210254 A1 | 11/2003 | Doan et al. |
| 2003/0215120 A1 | 11/2003 | Uppaluri et al. |
| 2004/0001094 A1 | 1/2004 | Unnewehr |
| 2004/0008809 A1 | 1/2004 | Webber |
| 2004/0066882 A1 | 4/2004 | Eberhard et al. |
| 2004/0066884 A1 | 4/2004 | Hermann Claus et al. |
| 2004/0066904 A1 | 4/2004 | Eberhard et al. |
| 2004/0094167 A1 | 5/2004 | Brady et al. |
| 2004/0101095 A1 | 5/2004 | Jing et al. |

(56) References Cited

U.S. PATENT DOCUMENTS

| | | |
|---|---|---|
| 2004/0109529 A1 | 6/2004 | Eberhard et al. |
| 2004/0171986 A1 | 9/2004 | Tremaglio, Jr. et al. |
| 2004/0267157 A1 | 12/2004 | Miller et al. |
| 2005/0049521 A1 | 3/2005 | Miller et al. |
| 2005/0063509 A1 | 3/2005 | Defreitas et al. |
| 2005/0078797 A1 | 4/2005 | Danielsson et al. |
| 2005/0089205 A1 | 4/2005 | Kapur |
| 2005/0105679 A1 | 5/2005 | Wu et al. |
| 2005/0113681 A1 | 5/2005 | DeFreitas |
| 2005/0113715 A1 | 5/2005 | Schwindt et al. |
| 2005/0129172 A1 | 6/2005 | Mertelmeier |
| 2005/0135555 A1 | 6/2005 | Claus et al. |
| 2005/0135664 A1 | 6/2005 | Kaufhold et al. |
| 2005/0140656 A1 | 6/2005 | McLoone |
| 2005/0226375 A1 | 10/2005 | Eberhard et al. |
| 2006/0026535 A1* | 2/2006 | Hotelling ............ G06F 3/0488 715/863 |
| 2006/0030784 A1 | 2/2006 | Miller et al. |
| 2006/0074288 A1 | 4/2006 | Kelly et al. |
| 2006/0098855 A1 | 5/2006 | Gkanatsios et al. |
| 2006/0129062 A1 | 6/2006 | Nicoson et al. |
| 2006/0155209 A1 | 7/2006 | Miller et al. |
| 2006/0291618 A1 | 12/2006 | Eberhard et al. |
| 2007/0030949 A1 | 2/2007 | Jing et al. |
| 2007/0036265 A1 | 2/2007 | Jing et al. |
| 2007/0076844 A1 | 4/2007 | Defreitas et al. |
| 2007/0223651 A1 | 9/2007 | Wagenaar et al. |
| 2007/0225600 A1 | 9/2007 | Weibrecht et al. |
| 2007/0242800 A1 | 10/2007 | Jing et al. |
| 2008/0019581 A1 | 1/2008 | Gkanatsios et al. |
| 2008/0021877 A1 | 1/2008 | Saito |
| 2008/0045833 A1 | 2/2008 | Defreitas et al. |
| 2008/0109740 A1 | 5/2008 | Prinsen et al. |
| 2008/0130979 A1 | 6/2008 | Ren et al. |
| 2008/0187095 A1 | 8/2008 | Boone |
| 2008/0262874 A1 | 10/2008 | Toshimutsu |
| 2008/0267467 A1 | 10/2008 | Sokulin et al. |
| 2009/0003519 A1 | 1/2009 | Defreitas et al. |
| 2009/0010384 A1 | 1/2009 | Jing et al. |
| 2009/0033522 A1 | 2/2009 | Skillman |
| 2009/0080594 A1 | 3/2009 | Brooks et al. |
| 2009/0080602 A1 | 3/2009 | Brooks et al. |
| 2009/0135997 A1 | 5/2009 | Defreitas et al. |
| 2009/0174663 A1 | 7/2009 | Rudd |
| 2009/0213034 A1 | 8/2009 | Wu et al. |
| 2009/0268865 A1 | 10/2009 | Ren et al. |
| 2009/0296882 A1 | 12/2009 | Gkanatsios et al. |
| 2009/0304147 A1 | 12/2009 | Jing et al. |
| 2010/0054400 A1 | 3/2010 | Ren et al. |
| 2010/0083154 A1 | 4/2010 | Takeshita |
| 2010/0086188 A1 | 4/2010 | Ruth et al. |
| 2010/0135558 A1 | 6/2010 | Ruth et al. |
| 2010/0194682 A1 | 8/2010 | Orr |
| 2010/0195882 A1 | 8/2010 | Ren et al. |
| 2010/0226475 A1 | 9/2010 | Smith et al. |
| 2010/0325088 A1 | 12/2010 | Hsieh et al. |
| 2011/0137132 A1 | 6/2011 | Gustafson |
| 2011/0270358 A1 | 11/2011 | Davis |
| 2011/0282686 A1 | 11/2011 | Venon |
| 2011/0314405 A1 | 12/2011 | Turner |
| 2012/0131498 A1 | 5/2012 | Gross et al. |
| 2012/0133600 A1 | 5/2012 | Marshall et al. |
| 2012/0154431 A1 | 6/2012 | Fram |
| 2012/0275656 A1 | 11/2012 | Boese et al. |
| 2013/0239063 A1 | 9/2013 | Ubillos |
| 2013/0259193 A1* | 10/2013 | Packard ............... A61B 6/502 378/37 |
| 2014/0013280 A1 | 1/2014 | Yoshioka et al. |
| 2014/0033126 A1 | 1/2014 | Kreeger |
| 2014/0123183 A1 | 5/2014 | Fujimoto |
| 2014/0140604 A1 | 5/2014 | Carton et al. |
| 2014/0143710 A1 | 5/2014 | Zhao |
| 2014/0282216 A1 | 9/2014 | Baker |
| 2014/0314205 A1* | 10/2014 | Carelsen ............... A61B 6/547 378/62 |
| 2015/0094581 A1 | 4/2015 | Butler |
| 2015/0260816 A1 | 9/2015 | Liang |
| 2015/0309712 A1 | 10/2015 | Marshall et al. |
| 2015/0317434 A1 | 11/2015 | Kondo |
| 2015/0374325 A1* | 12/2015 | Shimizu ............... A61B 6/4441 378/98 |
| 2016/0162163 A1 | 6/2016 | Park et al. |
| 2016/0166222 A1* | 6/2016 | Kim ................. A61B 6/0492 378/37 |
| 2016/0235386 A1* | 8/2016 | Schweizer ............ A61B 6/547 |
| 2016/0296185 A1* | 10/2016 | Gemmel ............... A61B 6/547 |
| 2016/0364122 A1 | 12/2016 | Shimomura |
| 2016/0367120 A1 | 12/2016 | Dupont et al. |
| 2017/0038914 A1 | 2/2017 | Kawagishi |
| 2017/0065238 A1 | 3/2017 | Smith et al. |
| 2018/0137385 A1 | 5/2018 | Ren |
| 2018/0211421 A1 | 7/2018 | Wicklein |
| 2019/0196662 A1 | 6/2019 | Mitchell |
| 2019/0221046 A1* | 7/2019 | Maeda ................. A61B 6/5264 |
| 2019/0325255 A1 | 10/2019 | Ren |
| 2020/0363877 A1 | 11/2020 | Mellett |
| 2020/0373013 A1 | 11/2020 | Cao |
| 2022/0015731 A1 | 1/2022 | Liu |
| 2022/0020475 A1 | 1/2022 | Chen et al. |
| 2022/0031262 A1* | 2/2022 | Cowles ................ A61B 6/467 |
| 2022/0172824 A1 | 6/2022 | Solis |
| 2023/0107616 A1* | 4/2023 | Saba ................... A61B 6/461 378/37 |

FOREIGN PATENT DOCUMENTS

| | | |
|---|---|---|
| EP | 982001 | 3/2000 |
| EP | 1004957 | 5/2000 |
| EP | 1428473 | 6/2004 |
| EP | 2783632 | 10/2014 |
| EP | 2913769 | 9/2015 |
| EP | 2952376 | 12/2015 |
| JP | 2000-322198 | 11/2000 |
| JP | 2004-038947 | 2/2004 |
| JP | 2004-357789 | 12/2004 |
| JP | 2007-029260 A | 2/2007 |
| JP | 2007-282656 | 11/2007 |
| JP | 2007-330374 | 12/2007 |
| JP | 2008-503253 | 2/2008 |
| JP | 2008-073436 | 4/2008 |
| JP | 2008-199293 | 8/2008 |
| JP | 2010-086149 | 4/2010 |
| JP | 2014-068874 | 4/2014 |
| JP | 2014-104099 | 6/2014 |
| JP | 2017-000664 | 1/2017 |
| WO | 1990/05485 | 5/1990 |
| WO | 1998/16903 | 4/1998 |
| WO | 00/51484 | 9/2000 |
| WO | 03/020114 | 3/2003 |
| WO | 2005/051197 | 6/2005 |
| WO | 2005/110230 | 11/2005 |
| WO | 2005/112767 | 12/2005 |
| WO | 2006/055830 | 5/2006 |
| WO | 2006/058160 | 6/2006 |
| WO | 2011/044295 | 4/2011 |
| WO | 2011/066486 | 6/2011 |
| WO | 2012/071429 | 5/2012 |
| WO | 2014/183183 | 11/2014 |
| WO | 2018/183548 | 10/2018 |
| WO | 2018/183549 | 10/2018 |
| WO | 2018/183550 | 10/2018 |
| WO | 2019/032558 | 2/2019 |
| WO | WO-2020068845 A1 * | 4/2020 ............ A61B 6/025 |

OTHER PUBLICATIONS

Cole, Elodia, et al., "The Effects of Gray Seale Image Processing on Digital Mammography Interpretation Performance", Academic Radiology, vol. 12, No. 5, pp. 585-595, May 2005.

Digital Clinical Reports, Tomosynthesis, GE Brochure 98/5493, Nov. 1998.

(56) References Cited

OTHER PUBLICATIONS

Dobbins JT et al. "Digital x-ray tomosynthesis: current state of the art and clinical potential" Physics in Medicine and Biology vol. 48, No. 19, pp. 65-81 (2003).
Essentials for life: Senographe Essential Full-Field Digital Mammography System, GE Health-care Brochure, MM-0132-05.06-ENUS, 2006.
Filtered Back Projection, (NYGREN) published May 8, 2007; URL: http://web.archive.org/web/1999101013 I 715/http://www.owlnet.rice.edu/-elec539/Projects97/cult/node2.html.
Grant, DG, "Tomosynthesis, a three dimensional imagine technique", IEEE Trans. Biomed Engineering, vol. BME-19, #1, Jan. 1972, pp. 20-28.
Heang-Ping Chan et al., "ROC study of the effect of stereoscopic imaging on assessment of breast lesions", Medical Physics, vol. 32, No. 4, Apr. 2005.
Kita et al., "Correspondence between different view breast X-rays using simulation of breast deformation", Proceedings 1998 IEE Computer Society Conference on Computer Vision and Pattern Recognition, Santa Barbara, CA, Jun. 23-25, 1998, pp. 700-707.
Lorad Selenia Document B-BI-SEO US/Intl (May 2006) copyright Hologic 2006.
Mammographic Accreditation Phantom, http://www.cirsinc.com/pdfs/015cp.pdf.
Pediconi, Federica et al., "Color-coded automated signal intensity curve for detection and characterization of breast lesions: Preliminary evaluation of a new software for MR-based breast imaging", International Congress Series 1281 (2005) 1081-1086.
Senographe 700 & 8OOT (GE); 2-page download on Jun. 22, 2006 from www.gehealthcare.com/inen/rad/whe/products/mswh800t.html.; Figures 1-7 on 4 sheets relateral shift compression paddle.
Smith, A., "Fundamentals of Breast Tomosynthesis", White Paper, Hologic Inc., WP-00007, Jun. 2008.

\* cited by examiner

INTERACTIVE MODEL INTERFACE FOR IMAGE SELECTION IN MEDICAL IMAGING SYSTEMS

CROSS-REFERENCE TO RELATED APPLICATIONS

This application claims the benefit of priority to U.S. Provisional Application No. 63/252,320 filed Oct. 5, 2021, which application is hereby incorporated in its entirety by reference.

INTRODUCTION

Medical imaging is used for visualizing the inner structures and conditions of the human body. In the context of breast imaging, medical imaging contemplates detection of cancerous cells in breast tissue. A plurality of different imaging processes, image acquisition parameters, and image processing techniques are used to enhance images for better detection of abnormal tissue. A significant number of different images may be taken of a single breast or of a single patient. A technologist taking these images must work efficiently and accurately to take the images. Imaging errors may necessitate follow-up imaging, thereby exposing the patient to excess radiation.

SUMMARY

Examples of the present disclosure describe systems and methods relating to a method for determining an imaging type, the method including: displaying a visual representation of a breast and a visual representation of a medical imaging system capable of imaging the breast, wherein the visual representation of the medical imaging system includes a visual representation of a compression mechanism and a visual representation of an x-ray detector; receiving an indication to move the visual representation of the medical imaging system to a position and an orientation relative to the visual representation of the breast; displaying the visual representation of the medical imaging system in the position and the orientation relative to the visual representation of the breast; based on the position and the orientation of the visual representation of the medical imaging system relative to the visual representation of the breast, determining an image type of the medical imaging system; displaying the image type; and automatically adjusting at least one component of the medical imaging system based at least in part on the determined image type. In an example, the method further includes acquiring, while the breast is compressed by the imaging system, an x-ray image of the breast according to the determined image type. In another example, the method further includes receiving an indication to rotate the visual representation of the breast. In yet another example, the indication to rotate the visual representation of the breast is associated with rotation relative to a vertical axis along a length of the visual representation of the breast. In still another example, the orientation of visual representation of the medical imaging system is tilted relative to the visual representation of the breast.

In another example of the above aspect, the visual representation of the medical imaging system includes two parallel lines. In an example, the indication to move the visual representation of the medical imaging system includes an indication to rotate the visual representation of the medical imaging system in one of a clockwise or counter-clockwise direction. In another example, the indication to move the visual representation of the medical imaging system is a click and drag. In yet another example, the position and the orientation of the visual representation of the medical imaging system aligns with a predetermined position and a predetermined orientation.

In another aspect, the technology relates to a user interface for breast imaging, the user interface including: a visual representation of a breast; a visual representation of a medical imaging system capable of imaging the breast, wherein the visual representation of the medical imaging system includes: a visual representation of a compression paddle of the imaging system; and a visual representation of an x-ray detector of the imaging system; wherein the visual representation of the compression paddle and the visual representation of the x-ray detector are rotatable and positionable relative to the visual representation of the breast; and wherein an image type is displayed, based on a position and an orientation of the visual representation of the medical imaging system relative to the visual representation of the breast. In an example, the visual representation of the breast is three-dimensional. In another example, the visual representation of the breast is rotatable. In yet another example, the visual representation of the breast deforms based on the position and the orientation of the visual representation of a compression paddle and the visual representation of the platform relative to the visual representation of the breast. In yet another example, the visual representation of the breast includes a visual representation of two breasts. In still another example, the visual representation of the medical imaging system includes two parallel lines.

In another example of the above aspect, the two parallel lines are fixed relative to each other. In an example, the visual representation of the compression paddle and the visual representation of the x-ray detector are rotatable and positionable relative to a predetermined position and a predetermined orientation. In another example, the predetermined position and the predetermined orientation are associated with a specific image type. In yet another example, the image type is selected from a group consisting of: craniocaudal (CC); mediolateral oblique (MLO); mediolateral (ML); exaggerated craniocaudal lateral (XCCL); exaggerated craniocaudal medial (XCCM); cleavage view (CV); lateromedial (LM); tangential (TAN); caudocranial from below (FB); axillary tail (AT); lateromedial oblique (LMO); superoinferior oblique (SIO); and inferomedial superolateral oblique (ISO).

In another aspect, the technology relates to an apparatus for breast imaging, the apparatus including: an x-ray source capable of selectively moving relative to a breast; an x-ray detector; a compression system for compressing the breast, the compression system disposed between the x-ray source and the x-ray detector; a display; a processor; and memory storing instructions that, when executed by the processor, cause the apparatus to perform a set of operations including: displaying, at the display, a visual representation of the breast, a visual representation of the compression system, and a visual representation of the x-ray detector; receiving an indication to move the visual representation of the compression system and the visual representation of the x-ray detector relative to the visual representation of the breast; displaying, at the display, the visual representation of the compression system and the visual representation of the x-ray detector in a position and an orientation relative to the visual representation of the breast, based on the indication; based on the position and the orientation of the visual compression system and the visual representation of the x-ray detector relative to the visual representation of the breast, determining an image type; and displaying, at the display, the image type.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

The accompanying figures illustrate one or more aspects of the disclosed methods and systems. In the appended figures, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label. Non-limiting and non-exhaustive examples are described with reference to the following figures.

While examples of the disclosure are amenable to various modifications and alternate forms, specific examples have been shown by way of example in the drawings and are described in detail below. The intention is not to limit the scope of the disclosure to the particular examples described. On the contrary, the disclosure is intended to cover all modifications, equivalents, and alternatives falling within the scope of the disclosure and the appended claims.

DETAILED DESCRIPTION

Various aspects of the disclosure are described more fully below, with reference to the accompanying drawings, which show specific example aspects. However, different aspects of the disclosure may be implemented in many different forms and should not be construed as limited to the aspects described herein; rather, these aspects are provided so that this disclosure will be thorough and complete and will fully convey the scope of the aspects to those skilled in the art. Aspects may be practiced as methods, systems, or devices. The following detailed description is, therefore, not to be interpreted in a limiting sense.

Breast cancer is one of the leading causes of cancer-related mortality of women. Abnormalities may be identified in the breast tissue by implementing one or more imaging techniques such as breast CT, breast tomosynthesis, and digital mammography. The imaging techniques are employed by emitting x-ray radiation from a source and detecting the radiation at a detector. A breast that is being imaged is placed between the source and the detector, and is typically compressed or immobilized therebetween. Placement and orientation of the source and detector relative to the breast may be adjusted. For example, different relative angles of radiation emitted through the breast may provide different view angles to view and/or assess an abnormality in the breast. The image types (otherwise referred to as image views) are based on the relative position and orientation of the source and detectors relative to the breast. Examples of image types include craniocaudal (CC), mediolateral oblique (MLO), mediolateral (ML), exaggerated craniocaudal lateral (XCCL), exaggerated craniocaudal medial (XCCM), cleavage view or "valley view" (CV), lateromedial (LM), tangential (TAN), caudocranial from below (FB), axillary tail (AT), lateromedial oblique (LMO), superoinferior oblique (SIO), inferomedial superolateral oblique (ISO), specimen, among others. Image types may be associated with one or more imaging modalities, such as conventional mammography, tomosynthesis, HD tomosynthesis, mammography/synthesis combination, HD combination, 2D contrast-enhanced, 2D contrast-enhanced combination, biopsy, quality control, etc.

Desired imaging type(s) are selected by a medical professional such as a technologist prior to imaging a breast with a medical imaging system. Traditionally, imaging type(s) are selected from a list of all available imaging types for a specific imaging modality. The list of image types may be provided as a list of images showing a breast relative to components of an imaging system (e.g., source and/or detector). This approach, however, requires the medical professional to scan through a list of options and navigate through different tabs on an interface. Additionally, by looking through a list of options, the medical professional needs to compare each list option with the configuration of the medical imaging system. Thus, the list format burdens the medical professional.

Accordingly, the present disclosure provides systems and methods for displaying, identifying, and selecting an image type for a medical imaging system. In an example, the present technology provides a user interface. The user interface includes a visual representation of a breast and a visual representation of a medical imaging system. The visual representation of the medical imaging system includes a visual representation of one or more of a detector, a source, and a compression paddle. The visual representation of the medical imaging system may be rotatable and positionable relative to the visual representation of the breast. Based on the relative position and orientation of the visual representation of the medical imaging system relative to the visual representation of the breast, an image type is determined. The image type may be displayed at the user interface. While the present disclosure is directed to breast imaging, the concepts and functions described herein are also applicable to imaging of other body parts (e.g., the abdomen, appendages such as arms and feet, etc.). Certain body parts, such as limbs, are more amenable to rotation thereof relative to a static imaging system. The systems and methods described herein that depict rotation of an imaging system relative to a static breast are equally applicable to rotation of a body part relative to a static imaging system; necessary or desirable modifications thereof would be apparent to a person of skill in the art upon reading this disclosure.

Figure 1A:
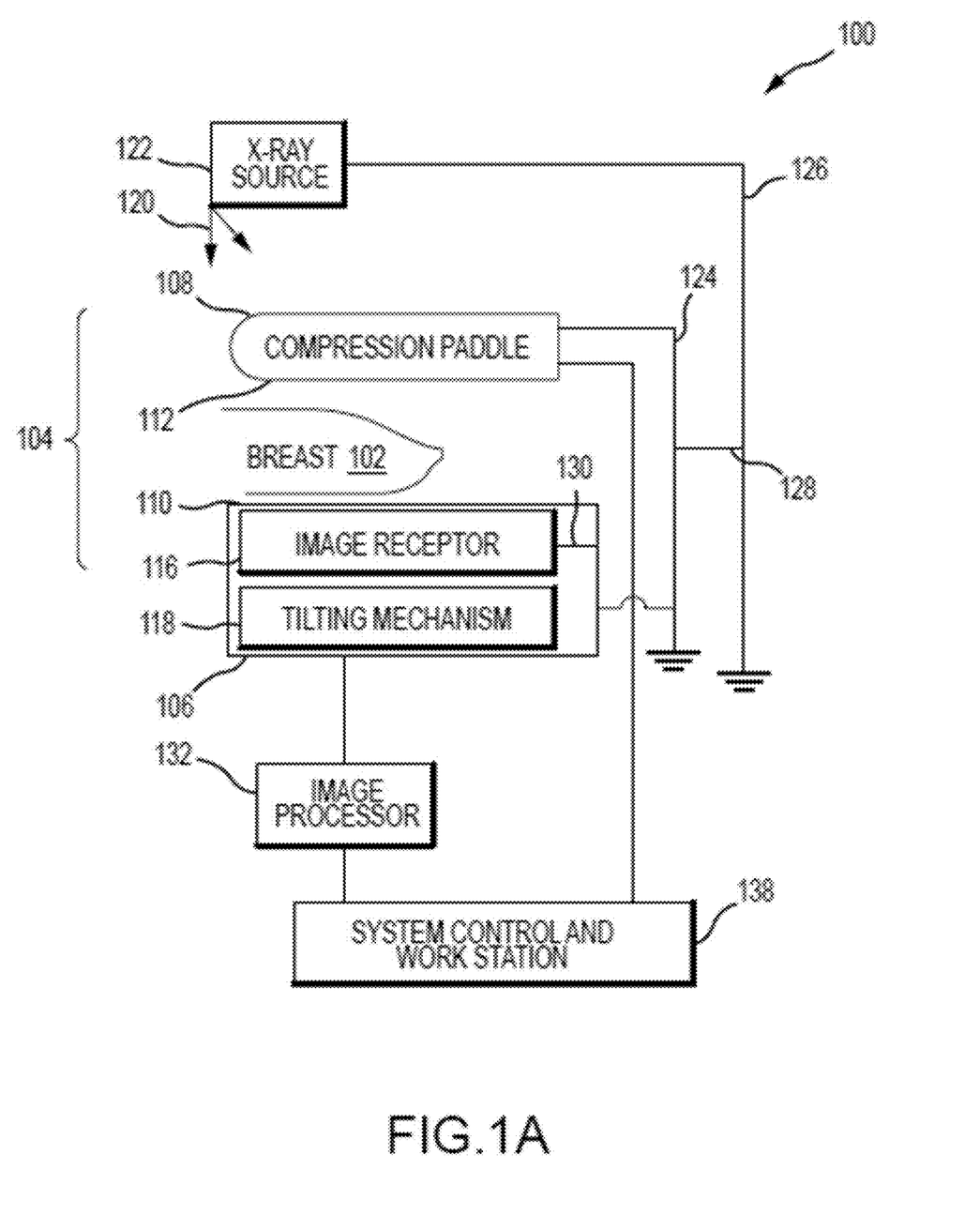
FIG. 1A depicts a schematic view of an example imaging system.
Figure 1B:
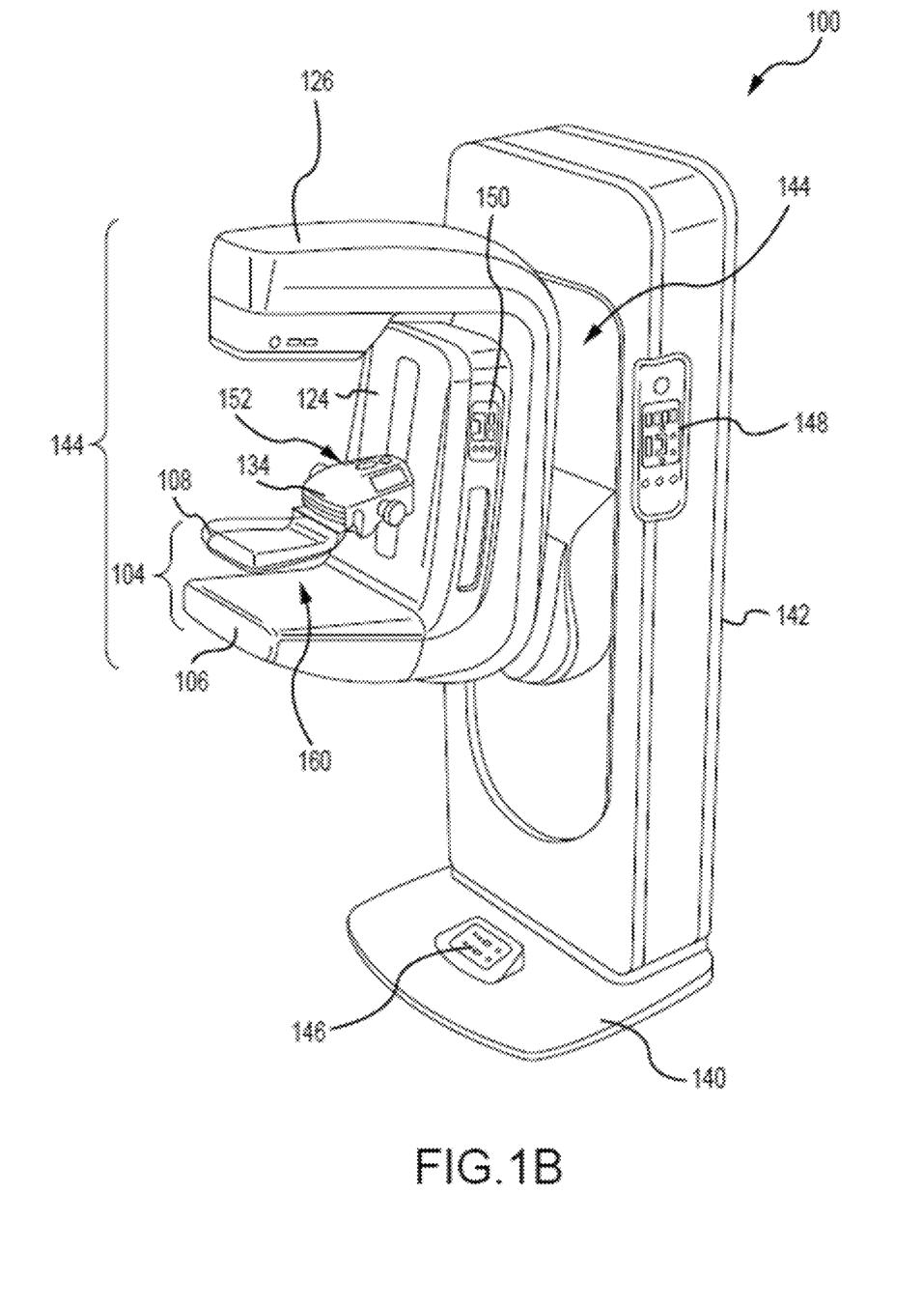
FIG. 1B depicts a perspective view of the example imaging system of FIG. 1A.

FIGS. 1A-1B show different views of an example imaging system 100. FIG. 1A depicts a schematic view of the example imaging system 100 and FIG. 1B depicts a perspective view of the example imaging system 100. The descriptions provided herein may be applied to either an upright (shown) or prone (not shown) imaging system 100. For simplicity, the following discussion includes examples for use with an upright breast tomosynthesis imaging system (such as the Dimensions Breast Tomosynthesis imaging system provided by Hologic, Inc.).

The imaging system 100 immobilizes a patient's breast 102 for x-ray imaging (either or both of mammography and tomosynthesis) via a breast compression immobilizer unit 104 that includes a static breast support platform 106 and a foam compressive element 108. Different paddles, each having different purposes, are known in the art. Certain examples paddles are also described herein for context. The breast support platform 106 and the foam compressive element 108 each have a compression surface 110 and 112, respectively, that move towards each other to compress, immobilize, stabilize, or otherwise hold and secure the breast 102 during imaging procedures. In known systems, the compression surface 110, 112 is exposed so as to directly contact the breast 102. Compression surface 110 may be a rigid plastic, a flexible plastic, a resilient foam, a mesh or screen, and so on. Compression surface 112 is a lower surface of the foam compressive element 108. The platform 106 also houses an image receptor 116 and, optionally, a tilting mechanism 118, and optionally an anti-scatter grid (not depicted, but disposed above the image receptor 116). The immobilizer unit 104 (otherwise referred to herein as the compression system 104) is in a path of an imaging beam 120 emanating from x-ray source 122, such that the imaging beam 120 impinges on the image receptor 116.

The immobilizer unit 104 is supported on a first support arm 124 via a compression arm 134, which is configured to be raised and lowered along the support arm 124. The x-ray source 122 is supported on a second support arm, also referred to as a tube head 126. For mammography, support arms 124, 126 can rotate as a unit about an axis 128 between different imaging orientations such as craniocaudal (CC) and mediolateral oblique (MLO), so that the imaging system 100 can take a mammogram projection image at each orientation. (The terms front, lower, and upper pertain to using a CC imaging orientation, with the patient facing the front of the imaging system, although it should be understood that other imaging orientations, including MLO, are used with the same equipment.) In operation, the image receptor 116 remains in place relative to the platform 106 while an image is taken. The immobilizer unit 104 releases the breast 102 for movement of arms 124, 126 to a different imaging orientation. For tomosynthesis, the support arm 124 stays in place, with the breast 102 immobilized and remaining in place, while at least the second support arm 126 rotates the x-ray source 122 relative to the immobilizer unit 104 and the compressed breast 102 about the axis 128. The imaging system 100 takes plural tomosynthesis projection images of the breast 102 at respective angles of the imaging beam 120 relative to the breast 102.

Concurrently and optionally, the image receptor 116 may be tilted relative to the breast support platform 106 and in sync with the rotation of the second support arm 126. The tilting can be through the same angle as the rotation of the x-ray source 122 but may also be through a different angle selected such that the imaging beam 120 remains substantially in the same position on the image receptor 116 for each of the plural images. The tilting can be about an axis 130, which can but need not be in the image plane of the image receptor 116. The tilting mechanism 118 that is coupled to the image receptor 116 can drive the image receptor 116 in a tilting motion. For tomosynthesis imaging and/or CT imaging, the breast support platform 106 can be horizontal or can be at an angle to the horizontal, e.g., at an orientation similar to that for conventional MLO imaging in mammography. The imaging system 100 can be solely a mammography system, a CT system, or solely a tomosynthesis system, or a "combo" system that can perform multiple forms of imaging. An example of such a combo system has been offered by the assignee hereof under the trade name Selenia Dimensions.

When the system is operated, the image receptor 116 produces imaging information in response to illumination by the imaging beam 120 and supplies it to an image processor 132 for processing and generating breast x-ray images. A system control and workstation unit 138 including software controls the operation of the system and interacts with the operator to receive commands and deliver information including processed-ray images.

The imaging system 100 includes a floor mount or base 140 for supporting the imaging system 100 on a floor. A gantry 142 extends upwards from the base 140 and rotatably supports both the tube head 208 and a support arm 210. The tube head 126 and support arm 124 are configured to rotate discretely from each other and may also be raised and lowered along a face 144 of the gantry 142 so as to accommodate patients of different heights. The x-ray source 122 is disposed within the tube head 208. Together, the tube head 126 and support arm 124 may be referred to as a C-arm 124.

A number of interfaces and display screens are disposed on the imaging system 100. Additionally or alternatively, a number of interfaces and display screens are disposed at the workstation unit 138, which may be located outside of a room of other components of the imaging system 100. These include a foot display screen 146, a gantry interface 148, a support arm interface 150, and a compression arm interface 152. In general, the various interfaces 148, 150, and 152 may include one or more tactile buttons, knobs, switches, as well as one or more display screens, including capacitive touch screens with graphical user interfaces (GUIs) so as to enable user interaction with and control of the imaging system 100. In general, the foot display screen 146 is primarily a display screen, though a capacitive touch screen might be utilized if required or desired.

Figure 2:
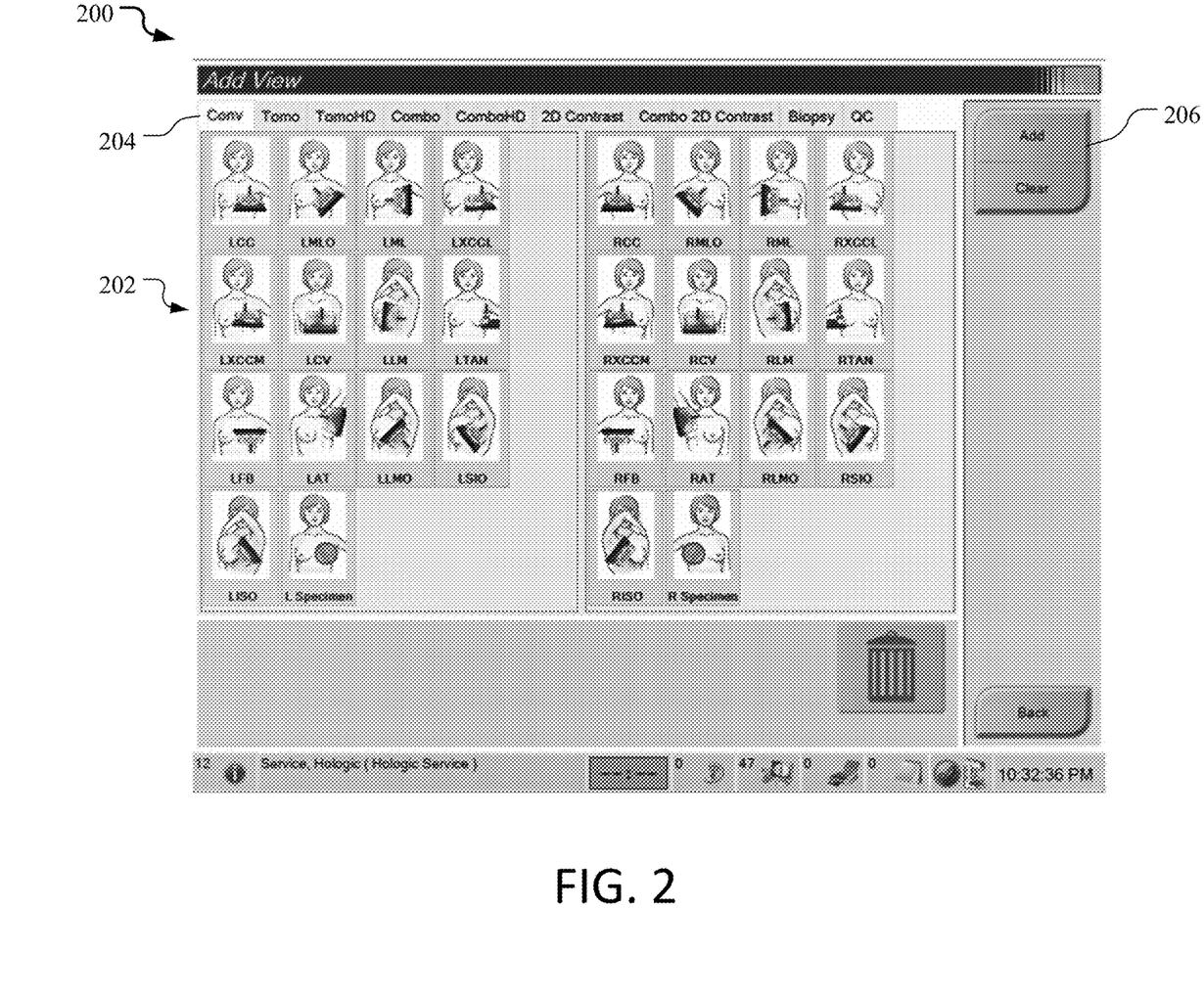
FIG. 2 depicts a prior art configuration of a user interface for selecting an image type for a medical imaging system.

FIG. 2 depicts a configuration of a user interface 200 for selecting an image type for a medical imaging system. The user interface 200 includes a set of image types 202, a set of image modalities 204, and imaging plan elements 206. The set of image types 202 includes a list of selectable image types on each tab for the set of image modalities 204. As shown, the "Conventional" modality tab is selected and shows a set of image types 202 organized by left and right breast imaging. Each tab for the set of image modalities 204 may include a different set of image types 202 associated with the selected tab. The imaging plan elements 206 include an "Add" element and a "Clear" element to add or remove one or more image types to a list. In an example, a medical professional using the user interface 200 may add one or more image types into a plan prior to imaging a breast. The image types may all be added to the plan before position the breast or after positioning the breast, or one or more image types may be added after positioning the breast for each image type.

Figure 3:
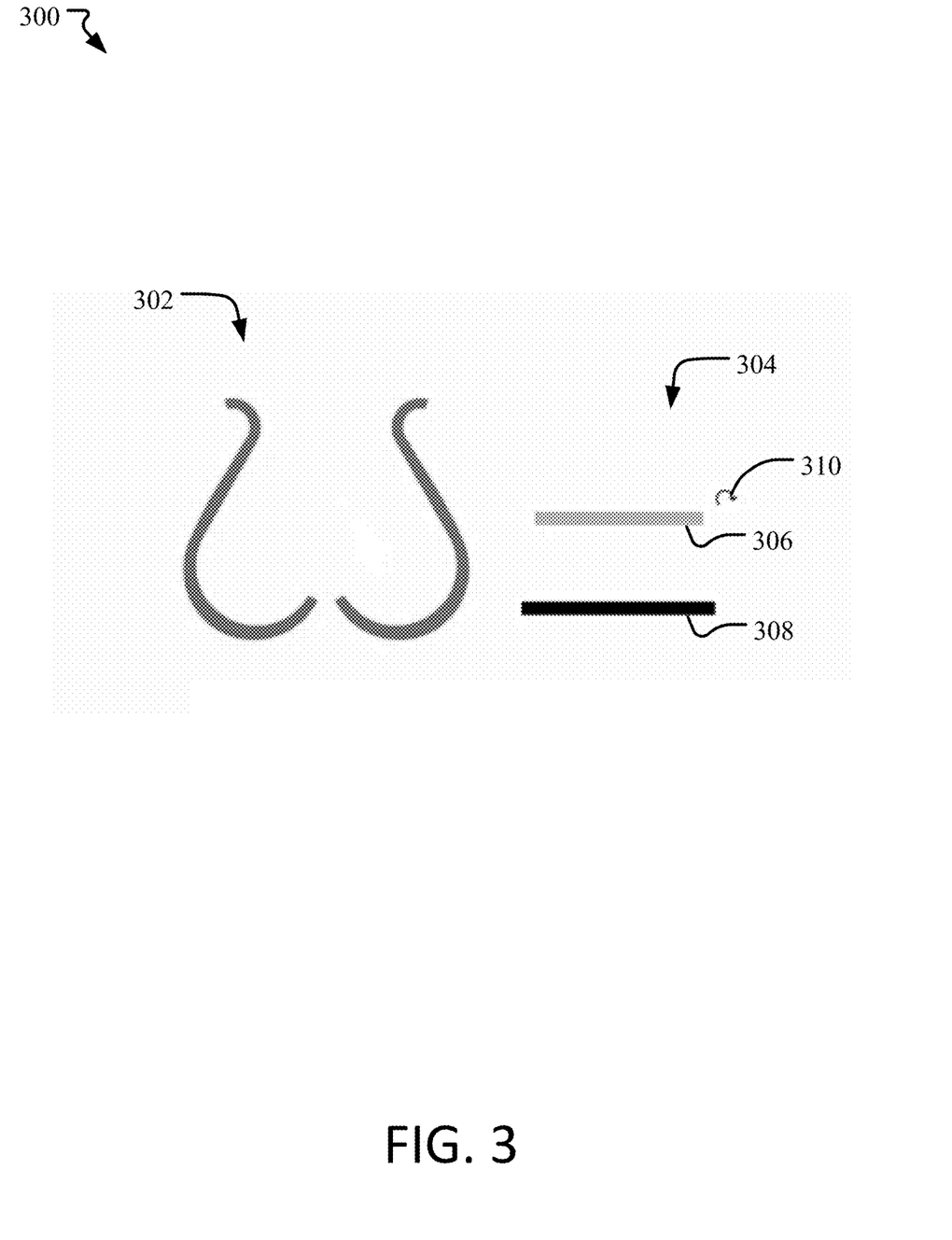
FIG. 3 depicts an example user interface for a medical imaging system.
Figure 4A:
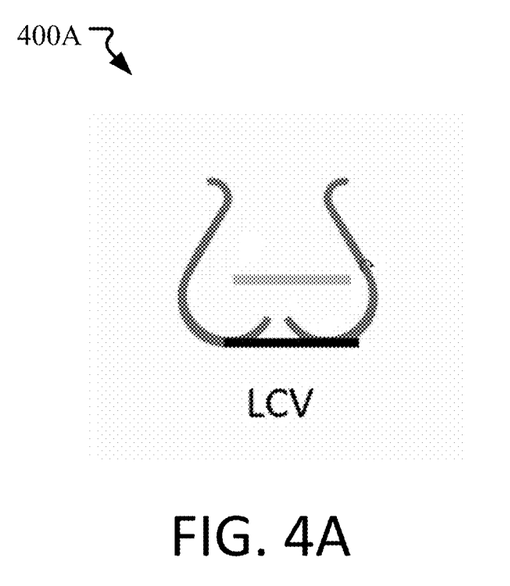
FIGS. 4A-4D depict different configurations of the example user interface of FIG. 3.
Figure 4B:
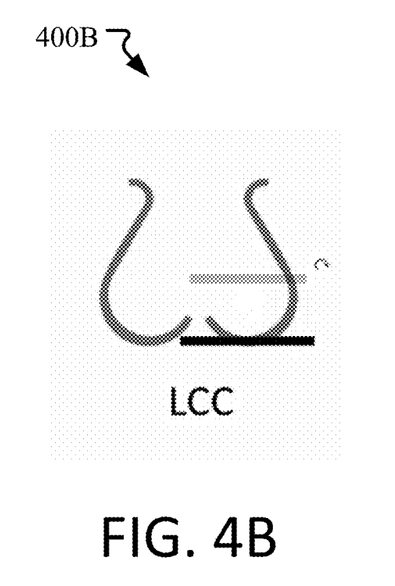
Figure 4C:
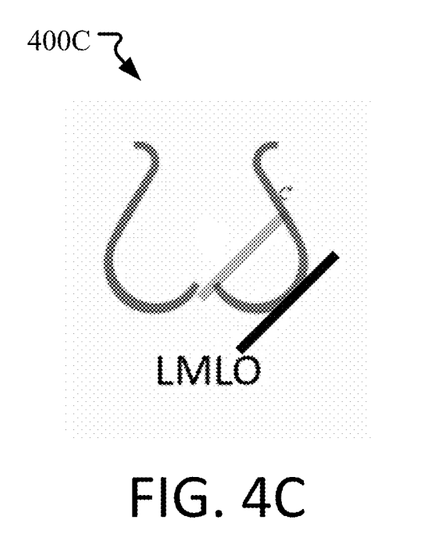
Figure 4D:
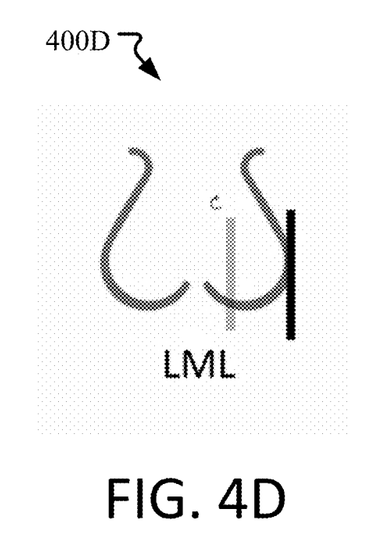

FIG. 3 depicts an example user interface 300 for a medical imaging system. The user interface 300 includes a visual representation of a breast 302 and a visual representation of a medical imaging system 304. The visual representation of the breast 302 may be two-dimensional or three-dimensional. Additionally, the visual representation of the breast 302 may rotate along an axis disposed substantially parallel to the user interface 300 (or of the screen on which the user interface is displayed). For example, the visual representation of the breast 302 may swivel or pivot about an axis representing a position of a spine of a patient. The visual representation of the breast 302 may change in shape to deform based on the relative position and orientation of the visual representation of the medical imaging system 304. For example, the visual representation of the breast 302 may deform to mimic deformation of breast tissue under compression by the imaging system. The visual representation of the breast 302 may include visual representations of one or two breasts. An example that might be more intuitive for a technologist, however, includes a visual representation of both breasts 302 of the patient, as depicted in FIG. 3. This representation of both breasts 302 may remain fixed in a position that is consistent with the patient standing or sitting at an imaging system, e.g., the representation of both breasts 302 does not rotate. By not rotating, this provides the technologist with a consistent frame of reference.

The visual representation of the medical imaging system 304 includes a visual representation of a detector 308 and a visual representation of one or more of a source 306 or a compression paddle 306 of the imaging system. In FIG. 3, a paddle 306 is depicted. In this regard, the representation of both the detector 308 and the paddle 306 is again intuitive for a technologist, since the breast contacts the paddle and detector (or support platform under which the detector is located) during imaging. Regardless, as further described herein, a specific source 306 may additionally or alternatively be visually represented. As further described herein, the visual representation of the medical imaging system 304 may be rotatable and positionable relative to the visual representation of the breast 302. This may be the most intuitive configuration for a technologist, since during most breast imaging procedures, the patient remains upright while the detector, source, and compression system of the imaging system rotate. The visual representation of a detector 308 and the visual representation of the source or paddle 306 may be fixed relative to each other or, alternatively, may be independently moved (e.g, towards or away from each other) or rotated. To rotate the visual representation of the medical imaging system 304, a rotation element 310 may be selected. Although one rotation element 310 is shown, multiple rotation elements may be appreciated (e.g., one for the visual representation of a detector 308 and one for the visual representation of the source or paddle 306 and/or one for the visual representation of the breast 302). Interaction with the rotation element 310 at the user interface 300 (e.g., a click, a click and drag, etc.) may result in rotation of the associated visually represented element. Rotation may be stepwise or may be based on an amount of drag or time with which the rotation element 310 is interacted. Rotation of a visually represented element may be about a center of the element or a predefined point on an element. Rotation may also be about a point predefined by an approximate midway point between the detector 308 and the source or paddle 306. Rotation may be clockwise or counterclockwise along an axis of rotation.

The visual representation of the medical imaging system 304 shown in FIG. 3 includes two, two-dimensional parallel lines representing the detector 308 and the source and/or paddle 306. The distance between the parallel lines may be fixed or variable and may by representative of the relative position of the detector to the compression paddle. Additionally, the visual representation of the medical imaging system 304 may be two-dimensional or three-dimensional. The dimensions of the visual representation of the medical imaging system 304 may be the same as or different than the visual representation of the breast 302. In an example, the visual representation of the breast 302 is three-dimensional and the visual representation of the medical imaging system 304 is two-dimensional. In another example, both the visual representation of the breast 302 and the visual representation of the medical imaging system 304 are three-dimensional. In a further example, both the visual representation of the breast 302 and the visual representation of the medical imaging system 304 are two-dimensional.

Based on the relative position and orientation of the visual representation of the medical imaging system 304 relative to the visual representation of the breast 302, an image type is determined. The image type may be determined based on predetermined zones or regions containing the visual representation of the medical imaging system 304. Alternatively, the position and orientation of the visual representation of the medical imaging system 304 may be compared to predetermined positions/orientations, with each position/orientation associated with a specific imaging type. In an example, the actual position/orientation of the visual representation of the medical imaging system 304 relative to the visual representation of the breast 302 is compared with the predetermined positions/orientations to determine which predetermined position/orientation is closest. The visual representation of the medical imaging system 304 may be moved or rotated based on a click and drag action. In an example, the visual representation of the medical imaging system 304 may snap to the nearest predetermined position/orientation upon release of the click and drag action. The image type may be displayed at the user interface. Additionally, based on the determined image type, an image of a real breast is captured while the breast is compressed or immobilized by the imaging system.

Elements on the user interface 300 may include controls, graphics, charts, tool bars, input fields, icons, etc. Alternatively, other suitable means for providing input may be provided at the medical imaging system or at the workstation, for instance by a wheel, dial, knob, keyboard, mouse, bezel key, or other suitable interactive device. Thus, commands associated with the user interface 300 may be accepted through a display as touch input or through other input devices. Inputs may be received by the medical imaging system from a medical professional. A variety of gestures may be supported by the user interface 300, including a swipe, double-tap, drag, touch and hold, drag and drop, etc. A drag gesture may include an uninterrupted selection and movement. For example, a drag may include movement of a touch interaction across a touch surface without losing contact with the touch surface. The drag gesture may be similar to a swipe gesture over a longer time and/or at a slower speed. As further described herein, a drag gesture at the user interface 300 may visually change a portion of the user interface 300, such as by rotating or moving the visual representation of the breast 302 or the visual representation of the medical imaging system 304.

FIGS. 4A-4D depict different configurations of the example user interface of FIG. 3. For example, a first configuration 400A shows the visual representation of the medical imaging system 304 in a horizontal position/orientation relative to the visual representation of the breast 302 that is associated with an LCV (or Left Cleavage View) image type. In another example, a second configuration 400B shows the visual representation of the medical imaging system 304 in a horizontal position/orientation relative to the visual representation of the breast 302 that is associated with an LCC (or Left Craniocaudal) image type. In another example, a third configuration 400C shows the visual representation of the medical imaging system 304 in a tilted position/orientation relative to the visual representation of the breast 302 that is associated with an LMLO (or Left Mediolateral Oblique) image type. In a further example, a fourth configuration 400D shows the visual representation of the medical imaging system 304 in a vertical position/orientation relative to the visual representation of the breast 302 that is associated with an LML (or Left Mediolateral) image type. Although only four configurations are shown, other configurations associated with other image types are contemplated. For example, FIG. 2 depicts a number of breast image types, as known in the conventional mammography modality. A representation of any known or developed image type in any known or developed imaging modality may be utilized.

In an example application, a doctor or other specialist may, prior to an imaging procedure, select one or more image types to be later obtained by a technologist who is working with the patient and the imaging system. The specialist may select one or more image types depending on a previously-identified region of interest that requires further investigation, a prior diagnosis, or a to investigate a new suspect location. In most examples, the specialist may select the representation from a predefined list of representations of image types (such as the image types depicted in FIG. 2 or as otherwise known in the art). These particular representations may be saved to the patient's record, then accessed by a technologist during the imaging procedure. The technologist may select the image on a workstation or on an imaging system itself. The imaging system may then adjust automatically the position of any number of components to place those components in the general position required to take the selected image type. For example, for a right mediolateral oblique (RMLO) image type, the breast support platform and detector may tilt to an angle consistent with such an image type, as would the compression paddle. A tube head containing the x-ray source may move to a position out of the way of the technologist as she assists in placing and compressing the breast. Adjustments to the position of the detector and/or compression paddle may be possible to fine tune positioning as required or desired to accommodate patient comfort, anatomy, height, etc. Thereafter, the patient's breast may be compressed and the imaging procedure may be performed. Subsequent to imaging and release of the breast from the imaging system, the technologist may select the next required representation and the imaging system may automatically position its components as required in preparation therefor.

Each image type in a predefined list of image types includes a representation of the breasts, a representation of the detector (relative to the breast), and a representation of the paddle and/or source (relative to the breast and the detector), along with an indicator of image type (e.g., RCC, LXCCL, RCV, etc.). The technologies described herein, however, contemplate a user interface that may reflect non-standard relationships between a representation of the breast and the representation of the detector and paddle and/or source. In such a system, the representation of the detector and paddle and/or source may be movable relative to the representation of the breast. As such, based on the user control described above, the user may move the representation of the detector and the paddle and/or source along an x-axis (e.g., between the right breast representation and the left breast representation), along a y-axis (e.g., higher or lower along the breast representation), and about a z-axis (e.g., a rotation position reflected in the angle of the detector representation relative to the breast representation). Information may be provided on the interface (such as detector angle) for future reference by the technologist when preparing the imaging system. The ability to move the representations in the x-, y-, and z-axes allows the representation of the breast to reflect easy-to-understand conditions, so a technologist may readily ascertain the type of image required or desired.

Although the user interface technologies described herein are described primarily in the context of breast imaging, imaging of other types of body parts are also contemplated. Breast imaging is a particular type of imaging that allows for movement of the imaging system (e.g., detector and source) to accommodate an otherwise static body part (e.g., the breast is not easy or comfortable to manipulate). As such, adjustment of the representations of the detector and paddle and/or source are about three axes, generally. In imaging procedures for other body parts that are more easily manipulated relative to imaging system, position and rotation of the body part relative to the detector. For example, if the detector on an imaging system is fixed (e.g., such as with a table-type imaging system), the representation of the body part itself may be manipulated within the user interface, e.g., with regard to both position and degree of rotation, while a representation of the detector remains fixed. Imaging information such as specific pre-defined image type, angle of rotation of the body part, or other information, may be provided on the user interface.

In one example, based on a particular imaging procedure, a series of image types may be preloaded as a way to walk the specialist through an imaging procedure. For example, for a routine screening exam, it is typical to perform bilateral craniocaudal (CC) and mediolateral oblique (MLO) views. For patients undergoing a diagnostic exam, additional views may be indicated. The series of image types may be preloaded onto the workstation and displayed to the specialist. The series may be based on the types of screening exam, patient's electronic medical record, the practice at the imaging facility, the geographic region of the imaging facility, and prescribed indications by a radiologist.

Figure 5:
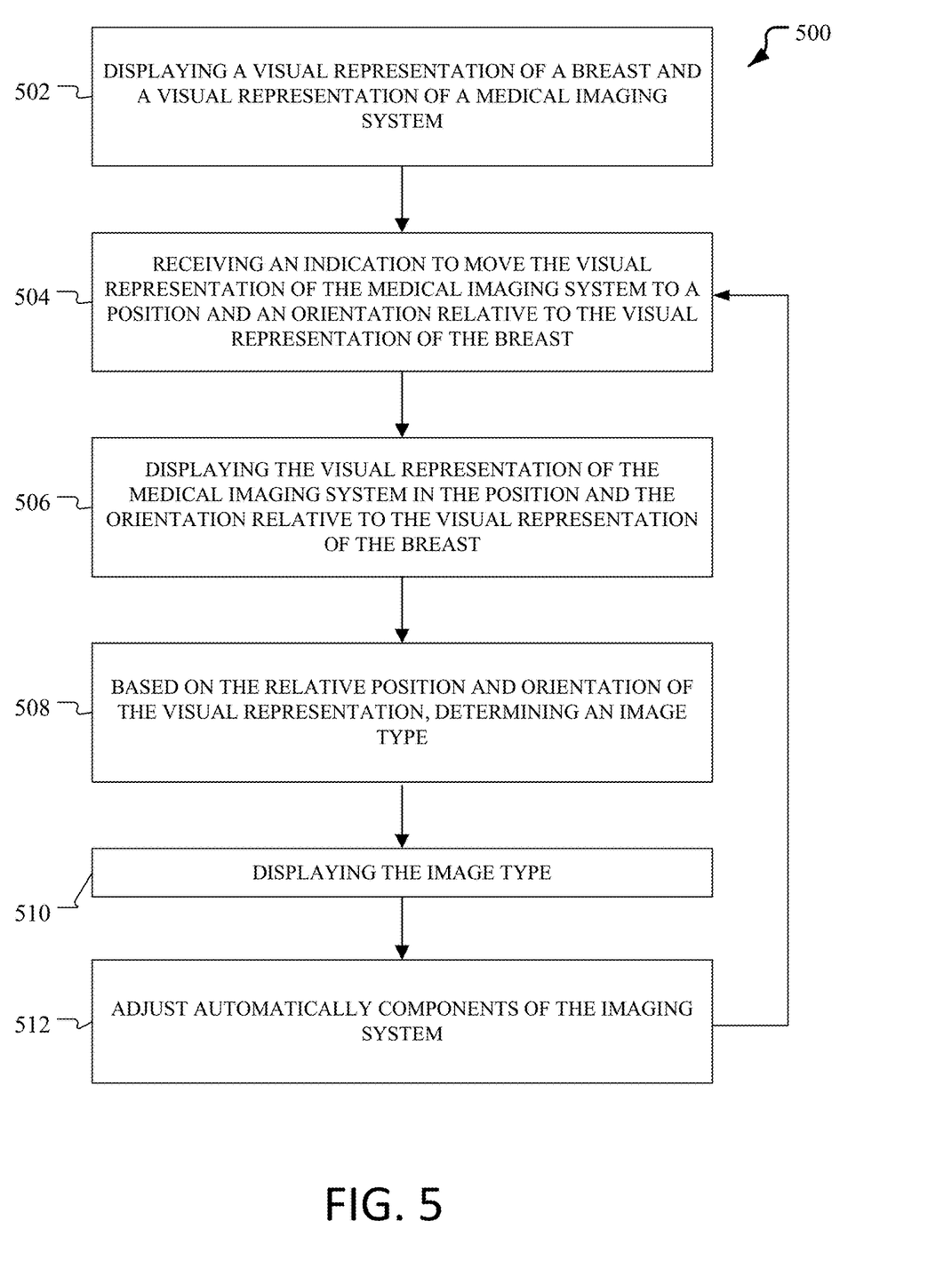
FIG. 5 depicts an example method for determining an image type for a medical imaging system.

FIG. 5 depicts an example method 500 for determining an image type for a medical imaging system. The method 500 may assist a user of an imaging system to determine an appropriate image type to image a breast, based on a configuration of the breast relative to the imaging system. The method 500 may be performed using systems described herein (e.g., imaging system 100 and user interface 300).

The method 500 begins at operation 502, where a visual representation of a breast and a visual representation of a medical imaging system are displayed. The display may be coupled to a medical imaging system or may be remote from a medical imaging system, such as at a remote workstation. The display shows a graphical user interface (GUI) that may have one or more features of the user interface 300 described with respect to FIG. 3. The visual representation of the medical imaging system may include visual representations of one or more components of the medical imaging system (e.g., the components shown in FIGS. 1A-1B of imaging system 100).

At operation 504, an indication to move the visual representation of the medical imaging system to a position and an orientation relative to the visual representation of the breast is received. The indication may be received at the GUI (e.g., via touch input) or may be received at a peripheral device connected to the display showing the GUI. In an example, movement and/or rotation of a visually represented element on the GUI may be a click and drag of the element. Visually represented elements being moved on the GUI may move relative to any received user input in real-time (e.g., an element moves according to a drag movement input).

At operation 506, the visual representation of the medical imaging system in the position and the orientation relative to the visual representation of the breast is displayed. The visual representation of the medical imaging system may snap to a closest position of a set of predetermined positions/orientations. For example, upon release of a click and drag input associated with the visual representation of the medical imaging system, the visual representation of the medical imaging system may be automatically re-positioned or re-oriented to align with a predetermined position/orientation. Each position/orientation of the set of predetermined positions may be associated with a unique image type.

At operation 508, an image type is determined based on the relative position and orientation of the visual representation. As further described herein, the image type may be based on which predetermined position/orientation is closest to the current position/orientation of the visual representation of the imaging system. Alternatively, the image type may be based on the current position/orientation of the visual representation of the medical imaging system being contained substantially within a predefined region or threshold. At operation 510, the image type is displayed. At operation 512, the imaging system may then adjust automatically the position of any number of components to place those components in the general position required to take the selected image type.

Operations 504-512 may repeat as required or desired. For example, if a visually represented element on the GUI is moved or reoriented relative to another visually represented element, the image type may be re-evaluated.

Figure 6:
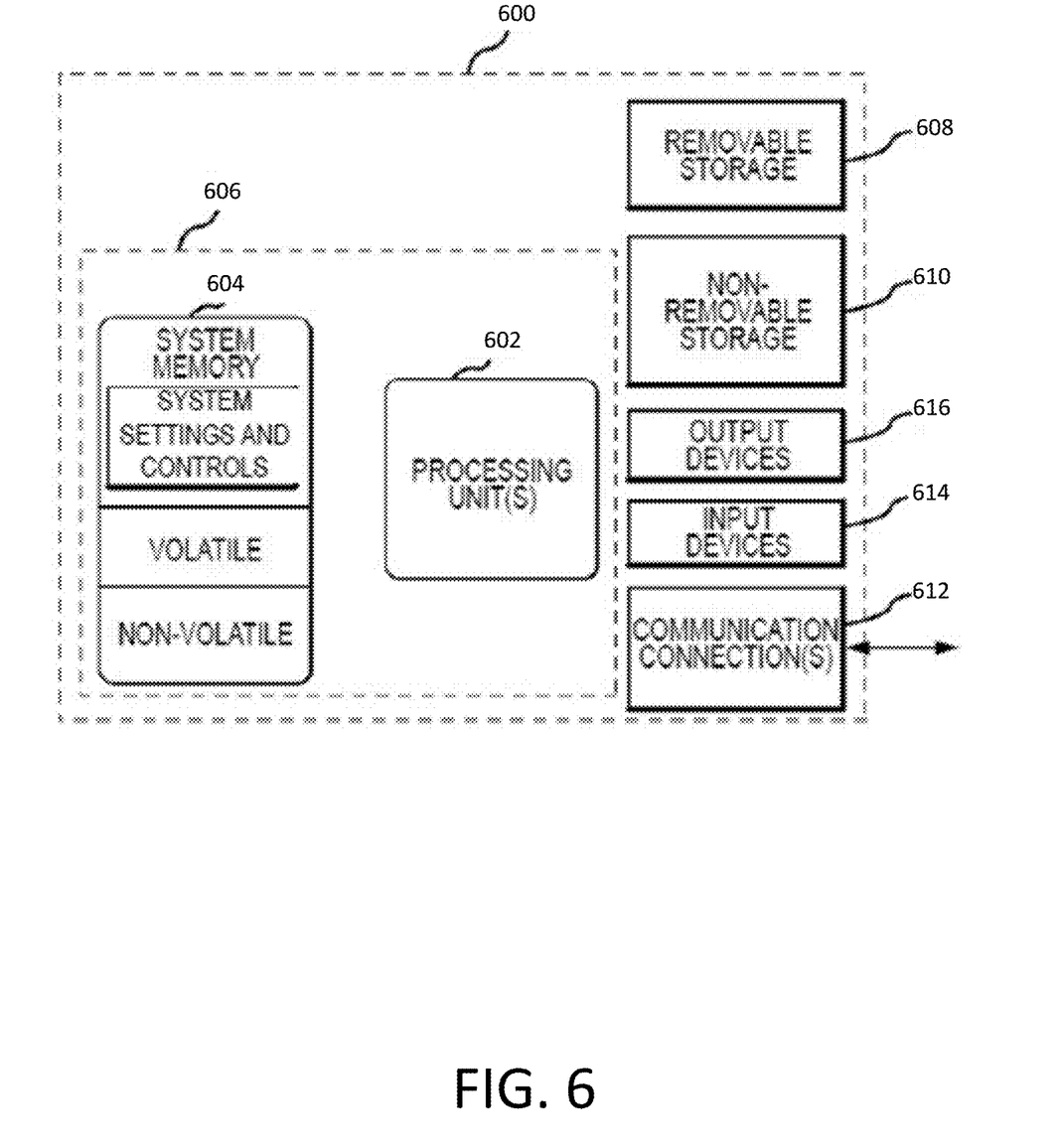
FIG. 6 illustrates an example operating environment for a medical imaging system.

FIG. 6 illustrates an example suitable operating environment 600 for a medical imaging system, as described herein. In its most basic configuration, operating environment 600 typically includes at least one processing unit (or processor) 602 and memory 604. Depending on the exact configuration and type of computing device, memory 604 (storing, instructions to perform projection of an image onto a specimen) may be volatile (such as RAM), non-volatile (such as RAM, flash memory, etc.), or some combination of the two. This most basic configuration is illustrated in FIG. 6 by dashed line 606. Further, environment 600 may also include storage devices (removable, 608, and/or non-removable, 610) including, but not limited to, magnetic or optical disks or tape. Similarly, environment 600 may also have input device(s) 614 such as keyboard, mouse, pen, voice input, etc. and/or output device(s) 616 such as a display, speakers, printer, etc. Also included in the environment may be one or more communication connections 612, such as LAN, WAN, point to point, etc. In embodiments, the connections may be operable to facility point-to-point communications, connection-oriented communications, connectionless communications, etc.

Operating environment 600 typically includes at least some form of computer readable media. Computer readable media can be any available media that can be accessed by one or more processing units (or processors) 602 or other devices comprising the operating environment. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transitory medium which can be used to store the desired information. Computer storage media does not include communication media.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, microwave, and other wireless media. Combinations of the any of the above should also be included within the scope of computer readable media.

The operating environment 600 may be a single computer operating in a networked environment using logical connections to one or more remote computers. The remote computer may be a personal computer, a server, a router, a network PC, a peer device or other common network node, and typically includes many or all of the elements described above as well as others not so mentioned. As an example, the operating environment 600 may be shared between one or more imaging systems, such as imaging system 100. The logical connections may include any method supported by available communications media. Such networking environments are commonplace in offices, enterprise-wide computer networks, intranets, and the Internet.

Although aspects of the present disclosure are described with respect to image analysis of living breast tissue, it should be appreciated that the present disclosure may also be useful in variety of other applications, such as imaging excised breast tissue, other tissue, bone, living organisms, body parts, or any other object, living or dead.

As should be appreciated, while the above methods have been described in a particular order, no such order is inherently necessary for each operation identified in the methods. For instance, the operations identified in the methods may be performed concurrently with other operations or in different orders. In addition, the methods described above may be performed by the systems described herein. For example, a system may have at least one processor and memory storing instructions that, when executed by the at least one processor, cause the system to perform the methods described herein.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure.

This disclosure describes some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art. Further, as used herein and in the claims, the phrase "at least one of element A, element B, or element C" is intended to convey any of: element A, element B, element C, elements A and B, elements A and C, elements B and C, and elements A, B, and C.

Although specific embodiments are described herein, the scope of the technology is not limited to those specific embodiments. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A method for determining an imaging type, the method comprising:
   displaying a visual representation of a breast and a visual representation of a medical imaging system capable of imaging the breast, wherein the visual representation of the medical imaging system includes a visual representation of a compression mechanism and a visual representation of an x-ray detector;
   receiving an indication to move the visual representation of the medical imaging system to a position and an orientation relative to the visual representation of the breast;
   displaying the visual representation of the medical imaging system in the position and the orientation relative to the visual representation of the breast;
   based on the position and the orientation of the visual representation of the medical imaging system relative to the visual representation of the breast, determining an image type of the medical imaging system;
   displaying the image type; and
   automatically adjusting at least one component of the medical imaging system based at least in part on the determined image type.

2. The method of claim 1, the method further comprising:
   acquiring, while the breast is compressed by the imaging system, an x-ray image of the breast according to the determined image type.

3. The method of claim 1, the method further comprising:
   receiving an indication to rotate the visual representation of the breast.

4. The method of claim 3, wherein the indication to rotate the visual representation of the breast is associated with rotation relative to a vertical axis along a length of the visual representation of the breast.

5. The method of claim 1, wherein the orientation of the visual representation of the medical imaging system is tilted relative to the visual representation of the breast.

6. The method of claim 1, wherein the visual representation of the medical imaging system includes two parallel lines.

7. The method of claim 1, wherein the indication to move the visual representation of the medical imaging system includes an indication to rotate the visual representation of the medical imaging system in one of a clockwise or counter-clockwise direction.

8. The method of claim 1, wherein the indication to move the visual representation of the medical imaging system is a click and drag.

9. The method of claim 1, wherein the position and the orientation of the visual representation of the medical imaging system aligns with a predetermined position and a predetermined orientation.

10. A user interface for breast imaging, the user interface comprising:
    a visual representation of a breast;
    a visual representation of a medical imaging system capable of imaging the breast, wherein the visual representation of the medical imaging system includes:
       a visual representation of a compression paddle of the imaging system; and
       a visual representation of an x-ray detector of the imaging system;
    wherein the visual representation of the compression paddle and the visual representation of the x-ray detector are rotatable and positionable relative to the visual representation of the breast; and
    wherein an image type is displayed, based on a position and an orientation of the visual representation of the medical imaging system relative to the visual representation of the breast.

11. The user interface of claim 10, wherein the visual representation of the breast is three-dimensional.

12. The user interface of claim 11, wherein the visual representation of the breast is rotatable.

13. The user interface of claim 10, wherein the visual representation of the breast deforms based on the position and the orientation of the visual representation of a compression paddle and the visual representation of the x-ray detector relative to the visual representation of the breast.

14. The user interface of claim 10, wherein the visual representation of the breast includes a visual representation of two breasts.

15. The user interface of claim 10, wherein the visual representation of the medical imaging system includes two parallel lines.

16. The user interface of claim 15, wherein the two parallel lines are fixed relative to each other.

17. The user interface of claim 15, wherein the visual representation of the compression paddle and the visual representation of the x-ray detector are rotatable and positionable relative to a predetermined position and a predetermined orientation.

18. The user interface of claim 17, wherein the predetermined position and the predetermined orientation are associated with a specific image type.

19. The user interface of claim 10, wherein the image type is selected from a group consisting of:
    craniocaudal (CC);
    mediolateral oblique (MLO);
    mediolateral (ML);
    exaggerated craniocaudal lateral (XCCL);
    exaggerated craniocaudal medial (XCCM);
    cleavage view (CV);
    lateromedial (LM);
    tangential (TAN);
    caudocranial from below (FB);
    axillary tail (AT);

lateromedial oblique (LMO);

superoinferior oblique (SIO); and inferomedial superolateral oblique (ISO).

20. An apparatus for breast imaging, the apparatus comprising:

an x-ray source capable of selectively moving relative to a breast;

an x-ray detector;

a compression system for compressing the breast, the compression system disposed between the x-ray source and the x-ray detector;

a display;

a processor; and memory storing instructions that, when executed by the processor, cause the apparatus to perform a set of operations comprising:

displaying, at the display, a visual representation of the breast, a visual representation of the compression system, and a visual representation of the x-ray detector;

receiving an indication to move the visual representation of the compression system and the visual representation of the x-ray detector relative to the visual representation of the breast;

displaying, at the display, the visual representation of the compression system and the visual representation of the x-ray detector in a position and an orientation relative to the visual representation of the breast, based on the indication;

based on the position and the orientation of the visual compression system and the visual representation of the x-ray detector relative to the visual representation of the breast, determining an image type; and displaying, at the display, the image type.

\* \* \* \* \*